(12) United States Patent
Marzec

(10) Patent No.: US 6,216,282 B1
(45) Date of Patent: Apr. 17, 2001

(54) COMBINED SUNGLASSES AND HEADBAND

(76) Inventor: Vincent G. Marzec, 5220 Rogers Rd., Hamburg, NY (US) 14075

( * ) Notice: Subject to any disclaimer, the term of this patent is extended or adjusted under 35 U.S.C. 154(b) by 0 days.

(21) Appl. No.: 09/504,200

(22) Filed: Feb. 15, 2000

(51) Int. Cl.[7] .................................................. A61F 9/02
(52) U.S. Cl. ................................ 2/452; 2/12; 2/DIG. 11; 351/155
(58) Field of Search ........................... 2/10, 12, 15, 171, 2/425, 452, 249, 250, 909, DIG. 11; 351/155

(56) References Cited

U.S. PATENT DOCUMENTS

| 4,393,519 | * | 7/1983 | Nicastro | 2/12 |
| 4,621,378 | * | 11/1986 | Hatchman | 2/9 |
| 4,712,254 | * | 12/1987 | Daigle | 2/452 |
| 4,852,189 | * | 8/1989 | Duggan | 2/452 |
| 4,955,087 | * | 9/1990 | Perez et al. | 2/12 |
| 5,377,360 | * | 1/1995 | Fleitman | 2/181 |
| 5,771,500 | * | 6/1998 | Mayes | 2/452 |
| 5,946,734 | * | 9/1999 | Vogan | 2/412 |

* cited by examiner

Primary Examiner—John J. Calvert
Assistant Examiner—Katherine Moran

(57) ABSTRACT

A unique combination is disclosed comprising an elasticized headband having perspiration absorbing padding and a flexible sun lens, the sun lens being removably connected to the perspiration absorbing padding by hook and loop elements, the padding and configuration of the lens coacting to generally provide improved intersection of sun rays.

8 Claims, 3 Drawing Sheets

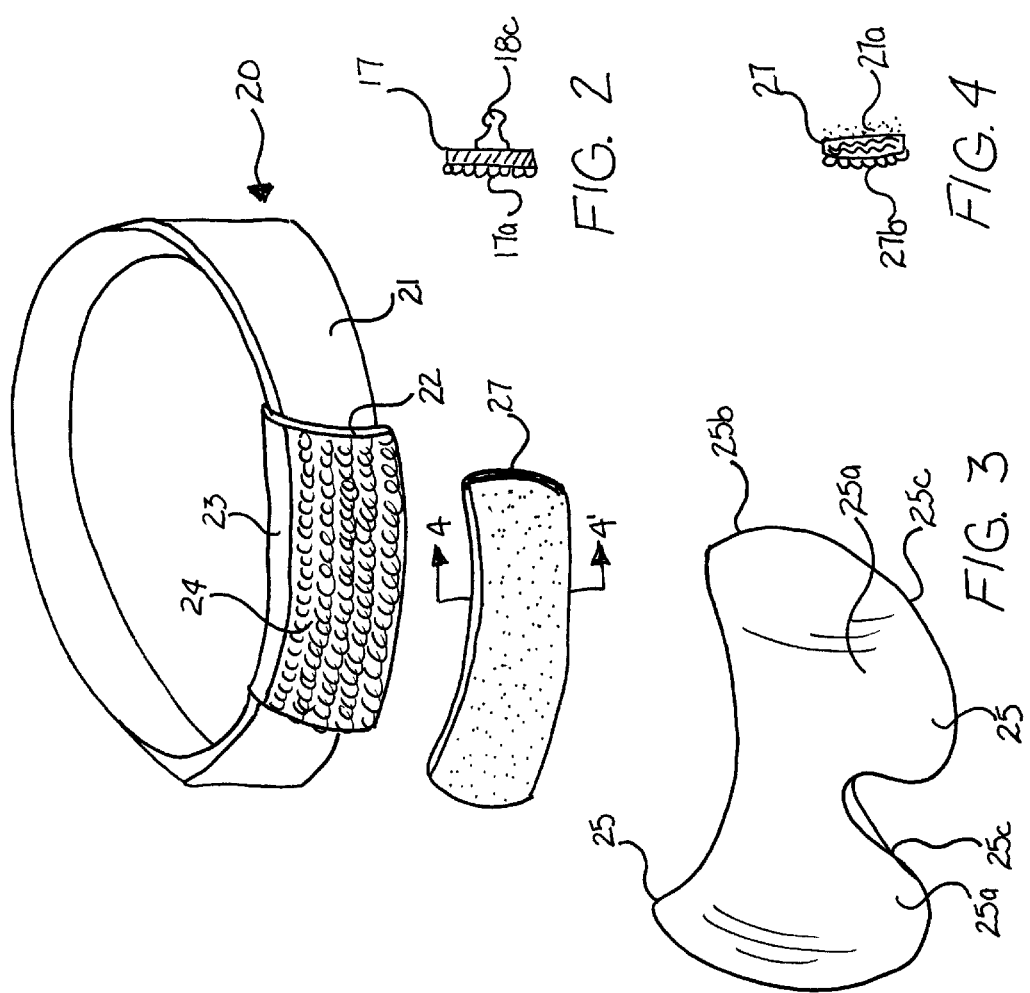

COMBINED SUNGLASSES AND HEADBAND

This invention relates to a unique combination of a stretchable headband with a detachable sunglass arrangement mounted thereto, the combination providing a unique surround to the eyes of the wearer for secure protection from sunlight during active sports wear.

BACKGROUND OF THE INVENTION

Sporting activities create differing problems in regard to the comfort and suitability of sunglasses as may be needed by a participant to protect the eyes from the effects of sunlight. In a typical physically active sport, occurring in sunlight which may negatively effect vision, the participant may be perspiring about the face and head, and the wearing of commonly available nose and ear supported sunglasses becomes problematic. Sunglasses slip from their common mounting places on sweaty noses and ears, requiring constant re-adjustment, complicated by perspiration forming along the participants brow and/or hands which may fog or otherwise be transferred onto the sunglasses lens, obscuring vision. Running, jumping and other jarring competitive activities only increase the problems and, particularly in situations wherein the participant is required to use his hands during the sporting activity, may disrupt the participant's ability to compete.

Various ways to solve such problems have been advanced. Sunlight intersecting lenses mounted in goggles are commercially available which generally provide an elastomeric and/or the like surround of the lens, the surround engaging the wearers face around the eye, with a tight band holding the device tightly to the wearers face. Goggles tend to form a dead air space in front of the eyes, which promote perspiration around the eyes and/or create an obscuring mist on the interior surface of the lens. Even though means have been advanced to enable some flow of air within goggles they are generally seen as being cumbersome, uncomfortable and vision obstructing, and thus have not enjoyed widespread acceptability as sunglass devices.

U.S. Pat. No. 4,955,087, discloses a device which comprises a combination visor and sunglass device. The device of this patent comprises a somewhat flexible plastic headband which comprises opposite ends which comprise buttons, buckles or the like for adjusting the headband size to a wearers head, the headband comprising a visor at the front position of the headband and a complex means for pivotally attaching a generally flat sunglass lens under the visor. The sunglass attachment means is arranged to enable pivoting the sunglass lens away from a position aligned opposite the eyes of the wearer during use to a position of non-use, aligned against the underside of the visor. Such device has been found acceptable for use in some sports related activities, but the pivoting nature of the lenses generally limits the design of the lens from intersecting sun rays from the side and the generally rigid nature of materials required for the pivot arrangement, sunvisor and the like, make the device cumbersome, uncomfortable and unsuitable for use in sports which may require running and jumping activity.

U.S. Pat. No. 5,105,475 discloses a device which is closely similar to U.S. Pat. No. 4,955,087, it too comprising a combination visor and sunglass. The device of this patent comprises a front headband area having spaced apart rigid walls for inserting an eyeshield therebetween and enabling a pivoting arrangement for the lens. As with U.S. Pat. No. 4,955,087, the pivoting arrangement of the device and the generally rigid nature of materials required for mounting the pivot arrangement, sunvisor and the like, the device is generally uncomfortable and unsuitable for use in many active sports.

It is an object of the present invention to provide a convenient, comfortable and simple sunglass arrangement which is particularly suitable for active sports wear.

It is another object of the present invention to provide a sunglass arrangement which surrounds the eyes of the wearer in such manner as to minimize entry of sunlight from the sides.

It is a further object of the present invention to provide a sunglass arrangement which resists the problem of vision interference by perspiration and/or fogging.

These and other objects of the invention will be apparent from the following description of the invention.

SUMMARY OF THE INVENTION

In its most general embodiment, the present invention comprises an elasticized headband, having perspiration absorbing, wear comfortable material on an inside surface thereof, together with an easily detachable somewhat rigid sun protecting lens. In its specific general embodiment, an elasticized headband comprises an outside surface containing a hook and/or loop configuration which is sized, arranged and/or spaced to engage a respective mating loop and/or hook configuration comprised on an inside surface of a somewhat flexible sun lens which enables a detachable mounting of the lens to the headband.

In one embodiment of the invention, the headband comprises a generally non-elasticized front portion having on its exterior surface the hook and/or loop configuration to which the mating hook and/or loop configuration of the inside surface of the lens engages. By the front portion of the headband is meant that portion of the headband which generally is arranged at about the forehead of the user. In a preferred embodiment, a generally non-elasticized front portion of the headband is padded, preferably with absorbing material, so that the exterior forward facing surface of the headband is spaced from the forehead. The padding provides additional comfort and perspiration protection to the user while positioning the sun lens spaced additionally outward from the forehead and thus further spaced from the eyes.

In still another embodiment, the headband comprises an elasticized band sheathed in a generally non-elasticized covering comprising the hook and/or loop surface. When not in use, the retraction of the elasticized band shirrs the non-elasticized sheath reducing the bulk of the device. When in use, the sheath de-shirrs sufficient to enable the user to mount the elasticized band around his head.

The sun lens generally comprises a tinted, polarized, darkened or the like, somewhat rigid material optically enabled to provide eye protection from the sun's rays. By somewhat rigid is meant that the lens is sufficiently rigid to retain its shape during use, but is also flexible enough to bend so as to generally conform to the shape of the attachment surface of the headband during use without breaking. In a preferred embodiment, the sun lens is comprised of a somewhat flexible material which can be curved, sized and dimensioned to have an upper inside surface which will matingly align with the front exterior surface of the headband, with the remaining portion of the lens extending downwardly opposite the eyes and arranged to intersect ambient sun rays before they enter the eyes. In one embodiment, the lens can be a generally flat panel with or without a notch for the nose. The panel can be curved to extend around the eyes to intersect ambient sun rays entering from about the side of the face. In a preferred embodiment, the panel is compound curved to extend inwardly toward the cheeks below the eyes and/or along the sides of the face to generally surround the eye. In a particularly preferred embodiment, a compound curved lens comprises a nose notch and the compound curves are arranged to such that the perimeter of the lens is closely spaced from engaging the face, being held in such closely spaced position by its attachment to the headband. In such arrangement, the lens intersects the suns ray's from engaging the eyes through almost all possible sight lines of the eye, without irritating contact with the skin of the user. In another such arrangement, the perimeter of the lens comprises a rounded bead to soften any contact with the skin and/or the nose notch comprises a padded and/or perspiration absorbing material to enable comfortable mounting of the lens on the nose.

The upper boundary of the sun lens comprises a border which is sized and dimensioned to have an upper inside surface which will matingly align with the front exterior surface of the headband. The upper inside surface of the lens comprises hook and/or loop material which is affixed to engage the mating loop and/or hook surface of the headband and hold the sun lens to the headband. In a preferred embodiment, the sun lens is formed to a slight curve generally conforming to the curvature of the forehead and comprises a somewhat flexible material. The hook and loop fastening means generally extends through a major portion of the width of the forehead. Thus, the headband generally mounts to the head above the eyebrows of the wearer and the sun lens generally extends from above the eyebrow of the wearer downwardly over the eyes of the wearer in such manner that sunlight cannot generally intersect with the eye from a position directly above the eye, without being blocked by the headband and/or intersecting the lens.

This arrangement is particularly comfortable for sports activities in that the wearer does not have to adjust his head and/or eyeshade his eyes to compensate for unshielded openings above the lens which otherwise occur with the common sunglasses. In this regard it is noted that the present invention obviates the need for sunglass visor combinations of the prior art by eliminating the need for a visor, while at the same time avoiding the inherent sight line narrowing limitations of a visor. Thus, in a sports activity which requires the following of the path of an object in the air above the horizon, the present invention solves the problem of sunlight interference with vision, without necessitating the wearing of peripheral vision limiting, protruding shading devices such as visors and the like.

In a similar manner, extension of a lens about the sides of the eyes obviates the necessity of head movement and/or shading to preclude interfering sunlight from entering the eye from the side. Interestingly, interference by sunlight from below the eyes is generally not of concern, however in the instance of a sporting activity wherein reflected light is of concern, such as snow skiing and the like adapting a preferred embodiment of the invention wherein the lens curves around below the eyes toward the face provides the desired protection.

BRIEF DESCRIPTION OF THE DRAWINGS

FIG. 2 is a sectional view of the loop strip of FIG. 1 of the invention taken along about line 2–2'.

FIG. 3 is an exploded perspective view illustrating another sun lens headband of the invention.

FIG. 4 is a sectional view of the loop strip of FIG. 3 of the invention taken along about line 4–4'.

DETAILED DESCRIPTION OF THE DRAWINGS

Figure 1:
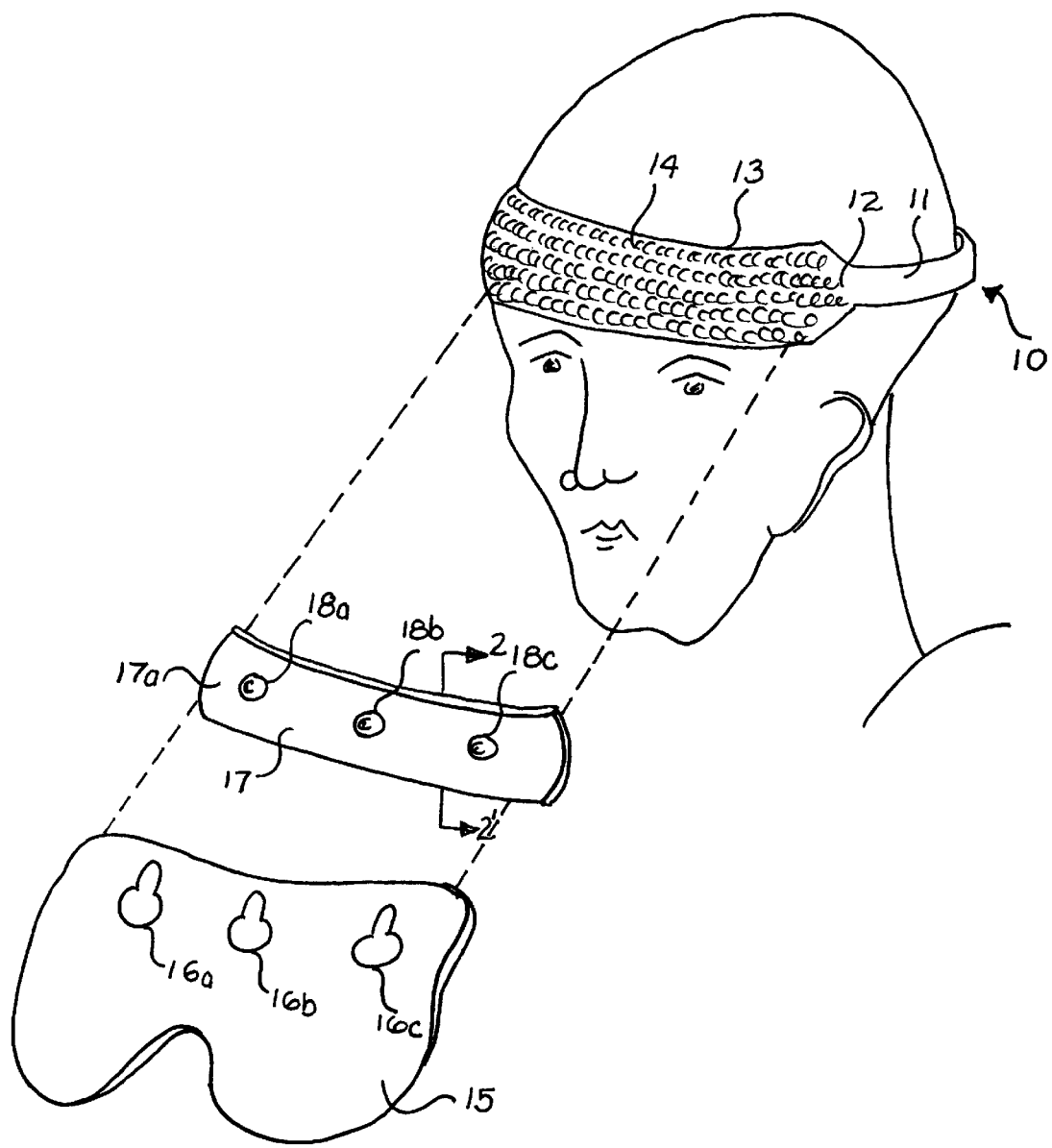
FIG. 1 is an exploded perspective view illustrating a sun lens headband of the invention.

Referring now to FIGS. 1 and 2, therein is illustrated, in exploded perspective, a sun lens headband arrangement of the invention. Therein headband 10, comprises elasticized band 11, which is fixedly attached 12 to perspiration pad 13. In this embodiment, perspiration pad 13 is illustrated as comprised of a soft, flexible, outer layer which engages the skin of the wearer, made from a loose woven material such as terry-cloth or the like, covering a fluid absorbing padding, the outer layer enabling the transmission of perspiration from the skin of the wearer to the interior of the pad. The forward facing surface 14 of pad 13 comprises a hook configuration for attachment of a mating loop configured material surface, the combination being generally known as Velcro attachment surfaces. In this embodiment, pad 13, elasticized band 11, and surface 14 are flexible and take the general curvature of the head upon which they are mounted.

Sun lens 15 is illustrated as comprising a somewhat flexible, generally transparent, curved plastic sheet which has been polarized, color spectrum blocked, tinted, coated or the like to provide the wearer relief to sun rays, glare and the like. In FIG. 1, an upper area of sun lens 15 is illustrated as comprising spaced mounting slots 16a–c. In FIGS. 1 and 2, loop strip 17 is illustrated as comprising spaced mounting studs 18a–c, and having a loop configured surface 17a arranged to engage hook surface 14 of pad 13. The studs may be mounted to the loop strip by any convenient adhesive or mechanical means. Spaced mounting studs 18a–c are arranged to matingly engage with spaced mounting slots 16a–c. Loop strip 17 engages along the inside surface of boundary 15a with the coacting stud and slot arrangement retaining loop strip 17 to the inside surface of the sun lens, with the loop configuration on surface 17b, arranged to matingly engage the hook configured surface 14 of pad 13. In a particularly preferred embodiment of the invention, flexible sun lens 15 is preformed to a curvature generally approximating the curvature of a forehead.

FIGS. 3 and 4 illustrate another embodiment of the invention wherein headband 20, comprises elasticized band 21, which is slidably mounted to perspiration pad 23. In this embodiment, perspiration pad 23 is illustrated as comprised of a soft, flexible padded material containing an interior slot 22 through which elasticized band 21 mounts, again the pad and elasticized band being flexible sufficient to take the general shape of the head upon which they are to be mounted. The forward facing surface 24 of pad 23 comprises a hook configuration for attachment of a mating loop configured surface. It should be understood, as with the embodiment of FIG. 1, the hook and loop configuration can be on either opposing surface of the pad and/or loop/hook strip.

Sun lens 25 is illustrated as comprising a somewhat flexible, generally transparent, compound curved plastic sheet which has been polarized, color spectrum blocked, tinted, coated or the like to provide the wearer relief to sun rays, glare and the like. In FIG. 3, sun lens 25 is illustrated as being significantly curved 25a so that its ends 25b, extend rearwardly to the side of the face beyond the length of the perspiration pad. The lower boundary 25c is illustrated as curved inwardly toward the face of the wearer. Similarly to FIG. 1, loop strip 27 is illustrated as comprising a surface 27a which engages the inside surface of the upper portion of the lens for mounting to sun lens 25, and an opposite surface 27b comprising a loop configuration for matingly engaging hook configured surface 24 of pad 23. Surface 27a of loop strip 27 is mounted to the inside surface of the lens upper boundary by adhesive, mechanical or the like suitable means.

In the embodiment of FIG. 3, the curvature of the lens around the side of the eyes and toward the face of the wearer provide a generally complete surround of the eyes, so that sun rays, glare and the like intersected by the lens from generally any direction.

Figure 5:
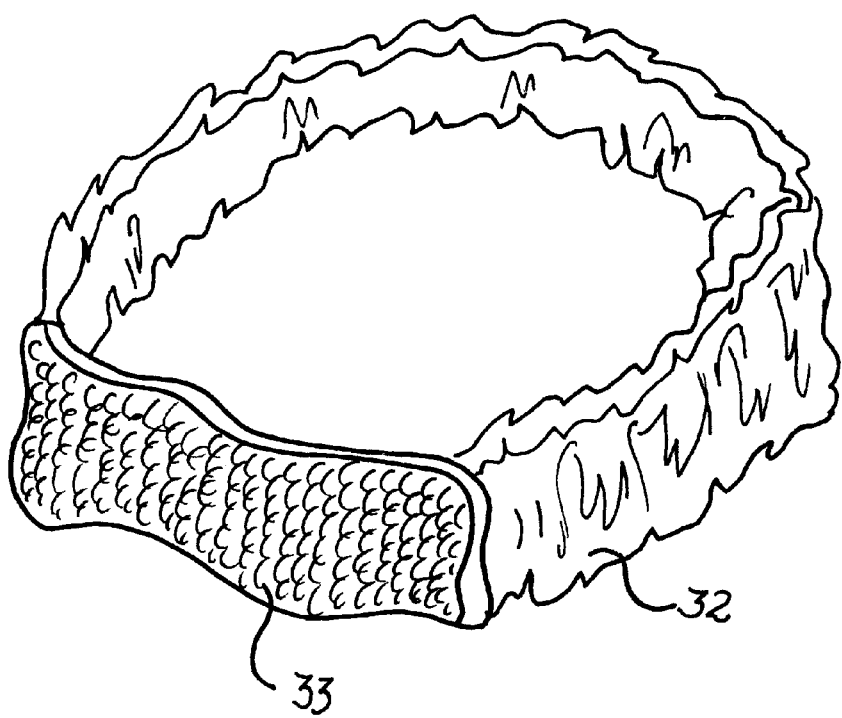
FIG. 5 is a perspective view of a further sun lens headband of the invention.

FIG. 5 provides still another embodiment wherein headband 30, comprises an elasticized band, which is covered by a cloth sheath 32 and comprises perspiration pad 33, having a hook and/or loop configured surface for mounting the sun lens (not shown). This embodiment, has particular appeal in that it enables convenient personalized design of the sheath and the material comprising the sheath can be perspiration absorbent for further protection.

I claim:

1. The combination comprising:

an elasticized headband, having a generally non-elasticized padded section slidably mounted thereon, said padded section having an outside surface containing a first hook and loop fastening element;

a flexible sun lens comprising an inside surface, said inside surface having a second hook and loop fastening element configured to mate and fasten to said first hook and loop fastening element;

wherein said second hook and loop fastening element is mounted adjacent an upper border of said sun lens, said padded section comprises a perspiration absorbing material, and said outside surface of said padded section extends forward from said elasticized band.

2. The combination of claim 1 wherein said second hook and loop fastening element is adhesively mounted to said inside surface of said sun lens.

3. The combination of claim 1 wherein said second hook and loop fastening element is mounted by mechanical means to said inside surface of said sun lens.

4. The combination of claim 3 wherein mechanical means comprises stud means which engage slot means in said sun lens.

5. The combination of claim 1 wherein said elasticized headband is covered by a cloth sheath.

6. The combination of claim 1 wherein said sun lens is curved such that its ends extend rearwardly to a side of a face of a wearer.

7. The combination of claim 1 wherein said sun lens is curved such that a lower boundary thereof extends inwardly toward a face of a wearer.

8. The combination comprising:

an elasticized headband having a generally non-elasticized padded section having an outside surface containing a first hook and loop fastening element;

a flexible sun lens comprising an inside surface, said inside surface having a second hook and loop fastening element configured to mate and fasten to said first hook and loop fastening element said sun lens comprising slot means arranged to engage stud means for mounting said sun lens to said second hook and loop fastening element;

wherein said second hook and loop fastening element is mounted adjacent an upper border of said sun lens, said padded section comprises a perspiration absorbing material, and said outside surface of said padded section extends forward from said elasticized band.

* * * * *